United States Patent [19]

Croudace

[11] Patent Number: 4,990,273

[45] Date of Patent: Feb. 5, 1991

[54] LUBRICATION ANTI-WEAR ADDITIVE

[75] Inventor: Michael C. Croudace, Santa Ana, Calif.

[73] Assignee: Union Oil Company of California, Los Angeles, Calif.

[21] Appl. No.: 122,519

[22] Filed: Nov. 20, 1987

Related U.S. Application Data

[63] Continuation-in-part of Ser. No. 781,966, Sep. 30, 1985, abandoned.

[51] Int. Cl.$^5$ ................ C10M 135/36; C07D 285/125
[52] U.S. Cl. .................................. 252/46.4; 252/47.0; 548/142
[58] Field of Search ................. 548/142; 252/46.4, 47

[56] References Cited

U.S. PATENT DOCUMENTS

| | | | |
|---|---|---|---|
| 2,685,588 | 8/1954 | Goshorn et al. | 252/47 |
| 2,690,999 | 10/1954 | Lowe et al. | 252/47 |
| 2,736,729 | 2/1956 | Krzikalla et al. | 548/142 |
| 2,760,933 | 8/1956 | Fields et al. | 548/142 |
| 2,764,547 | 9/1956 | Fields | 252/47 |
| 2,765,289 | 10/1956 | Fields et al. | 252/47 |
| 2,749,311 | 6/1956 | Sabel et al. | 252/47 |
| 2,910,439 | 10/1959 | Fields | 252/47 |
| 2,983,715 | 5/1961 | Fields | 548/142 |
| 3,663,561 | 5/1972 | Blaka | 252/47 |
| 3,909,420 | 9/1975 | Turnquest | 252/47 |
| 4,074,049 | 2/1978 | Begin et al. | 548/142 |
| 4,136,043 | 1/1979 | Davis | 252/47.5 |
| 4,167,059 | 8/1979 | King et al. | 252/47 |
| 4,246,126 | 1/1981 | Arakelian | 252/47.5 |
| 4,358,597 | 11/1982 | Felds | 252/47 |
| 4,412,928 | 11/1983 | Holstedt | 252/47 |
| 4,617,136 | 10/1986 | Doe, Jr. | 548/142 |
| 4,618,438 | 10/1986 | Toukan | 252/47.5 |
| 4,661,273 | 4/1987 | Frangalos | 252/47.5 |
| 4,678,592 | 7/1987 | Toukan | 548/142 |
| 4,704,426 | 11/1987 | Doe | 548/142 |
| 4,795,479 | 1/1989 | Karol | 548/142 |
| 4,902,804 | 2/1990 | King et al. | 548/142 |
| 4,925,580 | 5/1990 | Camenzind | 548/142 |

FOREIGN PATENT DOCUMENTS 0750907  6/1956  United Kingdom ................ 548/142

*Primary Examiner*—Olik Chaudhuri
*Assistant Examiner*—Ellen McAvoy
*Attorney, Agent, or Firm*—Gregory F. Wirzbicki; Arthur E. Oaks; Michael A. Kondzella

[57] ABSTRACT

An extreme pressure, anti-wear additive for lubricating compositions which is the reaction product of a 2,5-dimercapto-1,3,4-thiadiazole, an aldehyde and a primary or secondary, aliphatic or alicyclic amine.

48 Claims, No Drawings

LUBRICATION ANTI-WEAR ADDITIVE

This application is a continuation-in-part of application Ser. No. 781,966, filed 09/30/85, now abandoned.

BACKGROUND OF INVENTION

The present invention relates to an anti-wear additive for lubricating compositions and specifically to an extreme pressure, anti-wear additive.

Lubricating compositions reduce friction and reduce or prevent destructive contact between moving metal surfaces as long as a lubricating film is maintained between the moving surfaces. This particular type of lubrication is referred to as hydrodynamic lubrication.

Some anti-wear additives enhance the hydrodynamic lubrication of motor oils and the like. However, when the pressure and/or rubbing speeds between the moving metal surfaces increase, the lubricating film is forced out from between the moving metal surface. This results in metal-to-metal contact and wear. Lubrication under these extreme pressure conditions requires an additive that is adsorbed by or reacts with the metal to form an adherent protective film having a lower shear strength with the metal. This type of lubrication is needed under conditions called boundary lubrication, and additives enhancing this type of lubrication are known as "extreme pressure, anti-wear additives."

Many extreme pressure, anti-wear additives are known, with the most commercially used additives being phosphorus containing compounds, such as dialkyldithiophosphates. While these phosphorus-containing compounds provide a high degree of boundary lubrication, there is a move away from these types additives, especially for use in internal combustion engines because of the belief that, when these compounds or their oxidation products are carried by the exhaust gases, they react with and reduce the life of emission control catalysts.

Various types of other extreme pressure, anti-wear additives are known, such as the boron-containing compounds disclosed in U.S. Pat. Nos. 2,975,135; 3,509,054; 3,347,793; 3,356,707 and 4,115,286. While these boron-containing compounds provide some degree of boundary lubrication, other additives of similar or superior properties to the dialkyldithiophosphates are still being sought, and particularly those which will not poison or otherwise interfere with automotive emission control catalysts.

Certain derivatives of 2,5-dimercapto-1,3,4-thiadiazole have been disclosed as useful in lubricating compositions as corrosion inhibitors, such as the reaction product of a diamine and 2,5-dimercapto-1,3,4-thiadiazole (U.S. Pat. No. 2,910,439) and the reaction product of formaldehyde, a diaryl amine and 2,5-dimercapto,1,3,4-thiadiazole (U.S. Pat. No. 2,765,289). Other derivatives of 2,5-dimercapto-1,3,4-thiadiazole used as corrosion inhibitors in lubricating compositions are reaction products with an unsaturated ketone (U.S. Pat. No. 2,799,652); with an unsaturated cyclic compound (U.S. Pat. No. 2,764,547) and with formaldehyde and alcohol (U.S. Pat. No. 2,850,453). Also disclosed as corrosion inhibitors are thiadiazolyl dithiocarbamates (U.S. Pat. No. 2,690,999) and the carboxylic ester derivatives (U.S. Pat. No. 2,760,933).

SUMMARY OF THE PRESENT INVENTION

The present invention resides in an extreme pressure, anti-wear additive which is the reaction product of 2,5-dimercapto-1,3,4-thiadiazole with a compound possessing an oil solubilizing radical.

Preferably, the anti-wear additive of the invention is a reaction product of 2,5-dimercapto-1,3,4-thiadiazole, an aldehyde and a primary or secondary aliphatic or alicyclic amine. The preferred reaction product has the following general formula:

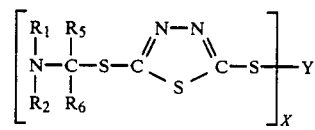

wherein:
X is an integer;
Y is hydrogen; a Group Ia, IIa, Ib metal, a transition metal or an amino radical of the formula:

$R_1$, $R_2$, $R_3$, and $R_4$ are the same or different and are hydrogen or a radical derived from an aliphatic or alicyclic compound with the total number of carbon atoms of $R_1+R_2$ being from about 8 to about 100 and the total number of carbon atoms of $R_3+R_4$ being from about 8 to about 100; and $R_5$, $R_6$, $R_7$, and $R_8$ are the same or different organic radical or hydrogen, with the total number of carbon atoms of $R_5+R_6$ being from 0 to about 20 and the total number of carbon atoms of $R_7+R_8$ being from 0 to about 20.

The present invention further resides in a method of enhancing the extreme pressure, anti-wear characteristics of a lubrication composition comprising an oleaginous material, such as a lubricating oil or grease, by admixing into the composition a sufficient amount of at least one 2,5-dimercapto-1,3,4-thiadiazole derivative reaction product. The invention also resides in the resulting lubricating composition.

DESCRIPTION OF THE PREFERRED EMBODIMENTS

Among the 2,5-dimercapto-1,3,4-thiadiazole derivatives suitable herein for enhancing the extreme pressure, anti-wear property of lubricating compositions are the oil soluble derivatives disclosed in U.S. Pat. Nos. 2,910,439; 2,765,289; 2,799,652; 2,764,547; 2,150,153; 2,690,999 and 2,760,933, all of which patents are incorporated herein by reference. The preferred 2,5-dimercapto-1,3,4-thiadiazole derivative reaction product of the invention may be prepared by reacting a 2,5-dimercapto-1,3,4-thiadiazole with at least one aldehyde and at least one primary or secondary, aliphatic or alicyclic amine in mole ratios of from about 1:1:1 to about 1:2:2, respectively, at a temperature in the range from about 25° C. to about 150° C. The total reaction time may range from about 0.5 hour to about 40 hours, and the reaction may be carried out in the presence or absence of a suitable solvent. Examples of suitable solvents are dioxane, hexane, dimethyl ether, diethyl ether or toluene.

The reaction may be carried out by either: (a) mixing all three reactants together; (b) reacting the aldehyde with the amine and subsequently reacting the thiadiazole with the product; or (c) reacting the aldehyde with the thiadiazole and subsequently reacting the amine with the product. At the completion of the reaction, both the solvent and the water-of-formation are typically removed by suitable methods, such as by stripping under vacuum. Preferably the water-of-formation is distilled off through an azeotrope trap during the progress of the reaction.

In one embodiment of the invention, the thiadiazole derivative reaction product is prepared by reacting the thiadiazole, aldehyde and amine at a 1:1:1 mole ratio, with this product further reacted with a metal or metal compound, preferably a Group Ia, IIa series metal or transition metal (collectively Groups Ib-VIIb and VIII as disclosed in the 60th ed. of the "*Handbook of Chemistry and Physics*, CRC Press, (1979)) or a compound comprising the same. It should be noted that the metal or metal compound should be in a form so as to be reactable with the thiadiazole derivative reaction product and that metals possessing a valence of two or more may be reacted at a mole ratio of greater than 1:1 with the thiadiazole derivative. For example, calcium or magnesium may be reacted at a 2:1 ratio with thiadiazole derivatives. Typically the metal is in the form of a metal salt, such as sodium or lithium salts, or in the metal halide or acetate, such as sodium chloride or acetate. Examples of suitable metals are sodium, potassium, magnesium and calcium.

Aldehydes which may be employed in the practice of the present invention are any of the $C_1$-$C_{20}$, preferably $C_1$-$C_{10}$, aliphatic, aromatic or alicyclic aldehydes. Suitable aldehydes may also contain substituents such as alkoxy, hydroxy, mercapto, nitro or halogen groups. Examples of suitable aldehydes are formaldehyde, acetaldehyde, benzaldehyde, 2-ethylhexylaldehyde, butyraldehyde, caprylicaldehyde, acrylicaldehyde, crotonaldehyde, vinylacetaldehyde, phenalacetaldehyde, nitrobenzaldehyde, furfural and chloral.

Amines which may be employed in the practice of the present invention are the $C_8$ to $C_{100}$, preferably $C_8$ to $C_{40}$, primary or secondary amines. Preferably the amine is a secondary amine. Examples of suitable amines are dihexylamine, dioctylamine, ditallowamine, dinonylamine, didodecylamine, dihexadecylamine, hexadecylamine, octadecylamine and dicyclohexylamine.

The preferred 2,5-dimercapto-1,3,4-thiadiazole derivative reaction product of the invention has the following general formula:

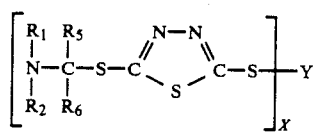

wherein:

X is an integer, more preferably one or two and most preferably one;

Y is hydrogen, a Ia, IIa, Ib metal, a transition metal or an amino radical of the following formula, and most preferably an amino radical of the following formula:

where $R_1$, $R_2$, $R_3$ and $R_4$ are the same or different and are hydrogen or a radical derived from a substituted or unsubstituted aliphatic or alicyclic compound (i.e. a nonaromatic radical), preferably an unsubstituted alkyl, alkenyl or alkynyl radical, and most preferably an unsubstituted alkyl or alkenyl radical, with the total number of carbon atoms of $R_1+R_2$ and $R_3+R_4$, independently, being from about 8 to about 100, preferably from about 8 to about 40; and where $R_5$, $R_6$, $R_7$, and $R_8$ are the same or different and are hydrogen or an organic radical, more preferably hydrogen or an organic radical derived from an aliphatic, alicyclic or aromatic compound, still more preferably hydrogen or an unsubstituted or substituted alkyl, aryl, araklyl, alkyloxy, aryloxy, aralkyloxy, alkenyl, alkenyloxy, alkynyl, alkynyloxy or aralkenyl radical, with the total number of carbon atoms of $R_5+R_6$ and $R_7+R_8$, independently, being from 0 to about 20, preferably from 0 to about 10, and most preferably hydrogen.

Lubricating compositions which may contain the additive of the invention include substantially all oleaginous materials such as lubricating oils or greases derived from mineral or synthetic oil or mixtures thereof. Lubricating oils may be of the naphthenic or paraffinic types, with mineral and synthetic oil of any suitable lubricating viscosity useful for the purposes of the present invention. In the case of greases, substantially any grease, e.g., metal soap grease, is improved in respect to its anti-wear properties and extreme pressure characteristics by the use of the additive of the invention The preferred oleaginous materials are lubricating oils for use in gasoline powered internal combustion engines, i.e., motor oils.

The thiadiazole derivative reaction product of the invention is incorporated into the lubricating oil or grease by blending or mixing, by any means, in a sufficient amount to enhance the extreme pressure anti-wear characteristics of the composition, as measured by means known to those skilled in the art, such as by ASTM Falex Test Method D2670-67 (reapproved 1977), herein incorporated by reference. The concentration of additive which will yield optimum results will depend upon the particular additive chosen and the particular oleaginous material into which it is introduced. The lubricating composition is provided with at least about 0.01 weight percent, preferably from about 0.25 to about 15 weight percent and most preferably from about 0.5 to about 2 weight percent of the thiadiazole derivative reaction product based upon the total amount of the oleaginous material and thiadiazole derivative reaction product.

The lubricating composition of the invention may also comprise other additives, such as corrosion inhibitors and antioxidants.

The following examples serve to further illustrate and instruct one skilled in the art in the best mode of practicing this invention and is not intended to be construed as limiting thereof.

EXAMPLE 1

One presently preferred additive of the invention was prepared as follows:

A mixture of 103 grams (g) of a mixture of $C_{16}$–$C_{18}$ secondary amines (0.2 moles) (marketed by Akzo Chemie America as "Armeen 2HT"), 15.02 g 2,5-dimercapto-1,3,4-thiadiazole (0.1 moles), 6.3 g paraformaldehyde (0.2 moles) and 30 milliliter (ml) of toluene was heated to reflux (about 111° C.), in a round flask equipped with a Dean Stark apparatus. The heated mixture was stirred for approximately hours with both water-of-formation and toluene distilled off and the water eliminated via the Dean Stark apparatus. After approximately 3.7 ml of water was distilled off, which approximately represented the stoichiometric amount of water-of-formation, the reaction was terminated and the remaining toluene vacuum distilled from the product. The final product was believed to be 2,5-dis(bisteryl-amino-ethyl-sulfide)-1,3,4-thiadiazole.

EXAMPLE 2

Another preferred additive of the invention was prepared as follows:

A mixture of 107.2 g of a mixture of $C_{16}$–$C_{18}$ primary amines (0.2 moles) (marketed by Akzo Chemie America as "Armeen TD"), 30.05 g 2,5-dimercapto-1,3,4-thiadiazole (0.2 moles), 12.6 g paraformaldehyde (0.2 moles) and 30 ml toluene were heated to reflux at about 111° C. in a round bottom flask equipped with a Dean Stark apparatus. While the reaction mixture was stirred and heated, water-of formation and toluene were co-distilled from the mixture for approximately 2 hours until about 8.5 ml water-of-formation was recovered, representing the approximate stoichiometric amount of water-of-formation. The reaction was terminated, and the remaining toluene vacuum distilled off, leaving 137.6 g of material believed to be 2,5-dis-(disterylaminomethyl sulfide)-1,3,4-thiadiazole.

EXAMPLE 3

Another preferred additive of the invention was prepared in a manner similar to those discussed above for Examples 1 and 2, with 0.2 moles of tallowamine used as the amine. For the purpose of the invention, the term "tallowamine" shall mean a mixture of amine consisting of approximately 29 percent hexadecyclamine, 20.5 percent octadecylamine, 44 percent of a mixture of octadecenylamine and octadecadienylamine, 3 percent tetradecylamine, 1.5 percent hexadecenylamine, 1 percent heptadecylamine and 0.5 percent tetradecenylamine. Tallowamine is produced commercially by the Armak Company under the tradename Armeen T.

EXAMPLE 4

A boron-containing, heterocyclic compound prepared, as taught in Example II of U.S. Pat. No. 4,490,265, by adding 17,605 grams of tallowamine and 15,362 grams of styrene oxide to a 65-liter round-bottomed flask that contains 11.34 liters of toluene and 1 liter of water. The flask is fitted with a water-cooled condenser and placed in a heating mantle. The mixture thus formed is refluxed at a moderate rate for 24 hours. The reaction is cooled to room temperature and 4,033 grams of boric acid are added to the flask. Next, the flask is fitted with a Dean-Stark trap, topped with a water-cooled condenser, and the reaction mixture is refluxed until water stops collecting the trap. Toluene is distilled from the reaction product to an end point temperature of 400° F. (204° C.). The reaction produces 34,695 grams of 1-hydroxy-3,7-diphenyl-5-tallow-5-aza-1-bora-2,8-dioxacyclooctane.

EXAMPLE 5

The procedures set forth above for Example 4 are repeated with the additional step of adding 0.96 g of sulfur and 75 ml of toluene to the flask containing the reaction product. The resulting mixture was heated to reflux and mixed for four hours, after which time the toluene is distilled off under vacuum leaving a sulfurized version of the product of Example 4.

EXAMPLES 6–12

Examples 6 through 8 were prepared by blending the 2,5-dimercapto-1,3,4-thiadiazole derivative reaction products of Examples 1, 2 and 3 into a 450 neutral oil at a treatment concentration to provide a 0.01645 molar solution (approximately 2.25 weight percent). Examples 9 and 10 were prepared by blending approximately 2.25 weight percent of the reaction products of Examples 4 and 5 into a 450 N oil, and Example 11 was prepared by blending 2.25 weight percent of a zinc dialkyldithiophosphate (a commercially available anti-wear additive sold by Amoco under the designation "Amoco 196") into a 450 neutral oil. These blends were then analyzed for anti-wear performance in comparison to a 450 neutral oil without an additive (Example 12) using the ASTM Falex Test Method D2670-67 (reapproved 1977). The Falex testing results for each example are listed below in Table 1 for the maximum load applied. The maximum load listed for Examples 6-8 was without the pin breaking, while the maximum load for Examples 9-12 was prior to the pin breaking. The higher the load a composition withstands, the better antiwear protection properties for that particular composition.

TABLE 1

| EXAMPLE NO. | MAXIMUM LOAD |
| --- | --- |
| 6 | 3,000 inch pounds |
| 7 | 4,000 inch pounds |
| 8 | 3,000 inch pounds |
| 9 | 950 inch pounds |
| 10 | 1,400 inch pounds |
| 11 | 1,250 inch pounds |
| 12 | 650 inch pounds |

As seen from the above Falex test results, lubricating compositions containing the thiadiazole derivative antiwear additive of the invention (Examples 6, 7 and 8) tolerate higher loadings without pin failure than did the blank composition Example 12 and given in comparison to the other anti-wear additives Examples 9, 10 and 11. The data show that, at the 2.25 weight percent level, the preferred additives of the invention enhance the antiwear protection of the 450 neutral oil by a factor of at least about 4.5 and are superior to the conventional zinc dialkyldithiophosphate by a factor of at least about 2.4.

As discussed above, the invention resides in one embodiment in a method of enhancing the extreme pressure, anti-wear characteristics of a lubricating composition comprising the admixing of a 2,5-dimercapto-1,3,5-thiadiazole derivative, such as those described in the above incorporated patents, into the composition. While it has been discovered in the invention that thiadiazole derivatives soluble in lubricating compositions should typically provide some enhancement of the extreme pressure, anti-wear characteristics of the lubricating composition, it has been found that the most preferred derivatives of 2,5-dimercapto-1,3,4-thiadiazole, an aldehyde and a primary or secondary aliphatic or alicyclic amine provide greater enhancement of the extreme pressure anti-wear characteristics than other such derivatives.

EXAMPLES 13-17

The following examples illustrate 2,5-dimercapto-1,3,4-thiadiazole derivatives other than the preferred. Examples 13-17 were prepared in accordance with the procedures set forth in U.S. Pat. No. 2,765,289, for Examples I-III, respectively to produce covalent compounds having the basic structure $$\begin{array}{c} R_1 \\ \diagdown \\ R_2 \end{array} N-CH_2-S-C \begin{array}{c} N-N \\ \diagup \diagdown \\ S \end{array} C-S-CH_2-N \begin{array}{c} R_3 \\ \diagup \\ R_4 \end{array}$$

wherein $R_1$, $R_2$, $R_3$ and $R_4$ radical for each example is listed in the following Table 2:

TABLE 2

| EXAMPLE NO. | R GROUP |
|---|---|
| 13 | (biphenyl) |
| 14 | (phenyl) |
| 15 | (p-octylphenyl) $-C_8H_{17}$ |

Examples 16 and 17 were prepared in accordance with the procedure of U.S. Pat. No. 2,910,439 for Examples I and IV to produce quaternary ammonium compounds having the basic structure $$\begin{array}{c} R_1 \ H \\ \diagdown | \\ N-S-C \\ \diagup | \\ R_2 \ H \end{array} \begin{array}{c} N=N \\ \diagup \diagdown \\ S \end{array} \begin{array}{c} H \ R_1 \\ | \diagup \\ C-S-N \\ | \diagdown \\ H \ R_2 \end{array}$$

wherein $R_1$ is a substantially C18 saturated aliphatic chain and in Example 16, $R_2$ is a substantially C18 saturated aliphatic chain and, in Example 17, $R_2$ is hydrogen. When attempts were made to form an anti-wear composition, similar to that of the present invention, by dissolving the compounds of Examples 13-17 in a 450 N oil, to a minimum addition level of 2.25 weight percent, it was found that only the derivative of Example 15 could be dissolved to this extent, the other compounds being essentially insoluble in this oil. To evaluate the anti-wear properties achieved, the thiadiazole derivative of Example 15 was blended in 450N oil to provide a 0.01645 molar solution (approximately 2.25 weight percent), and the resulting blend was analyzed for its anti-wear characteristics using the above referred to ASTM Falex Test Method, with the resulting maximum load prior to pin breaking being 1,020 inch pounds. This compares to the 3,000 and 4,000 inch pound results for Examples 6, 7 and 8 above without pin breakage and a 650 inch pound result for the 450N oil alone with pin breakage.

These results illustrate that the preferred thiadiazole derivatives of the invention as exemplified by Examples 1, 2 and 3 provide better anti-wear characteristics than other thiadiazole derivatives.

While the preferred embodiments have been described and illustrated, many modifications and variations may be made without departing from the scope of the invention. Accordingly, it is intended in the invention to encompass all such modifications and variations as fall within the spirit and scope of the appended claims.

I claim:

1. A method for enhancing the extreme pressure anti-wear characteristics of a lubricating composition comprising an oleaginous material, said method comprising admixing into said lubricating composition an extreme pressure anti-wear enhancing amount of a compound of the formula:

$$\left[ \begin{array}{c} R_1 \ R_5 \\ | \ | \\ N-C-S-C \\ | \ | \\ R_2 \ R_6 \end{array} \begin{array}{c} N-N \\ \diagup \diagdown \\ S \end{array} C-S \right]_x Y$$

wherein:
X is 1 or 2;
Y is hydrogen, a Ia, IIa, or Ib series metal, a transition metal or an amino radical of the formula:

$$\begin{array}{c} R_7 \ R_3 \\ | \ | \\ -C-N \\ | \ | \\ R_8 \ R_4 \end{array}$$

wherein:
$R_1$, $R_2$, $R_3$ and $R_4$ are the same or different and are hydrogen or a radical derived from an aliphatic or alicyclic compound with the total number of carbon atoms for $R_1 + R_2$ and $R_3 \ R_4$, independently being from about 8 to about 100; and $R_5$, $R_6$, $R_7$ and $R_8$ are the same or different and are hydrogen or an organic radical derived from an aliphatic, alicyclic or aromatic compound, wherein the total number of carbon atoms for $R_5 + R_6$ and $R_7 + R_8$, independently is from about 0 to about 20.

2. The method of claim 1 wherein Y is hydrogen.

3. The method of claim 1 wherein Y is the amino radical.

4. The method of claim 1 wherein Y is sodium, potassium, magnesium or calcium.

5. The method of claim 3 wherein the total number of carbon atoms for $R_5 + R_6$ and $R_7 + R_8$, independently, are from 0 to about 10.

6. The method of claim 5 wherein $R_5$, $R_6$, $R_7$ and $R_8$ are a substituted or unsubstituted alkyl, alkenyl, alkynyl, aryl, aralkyl, alkyloxy, alkenyloxy, alkynyloxy, arakyloxy, aryloxy or aralkenyl radical.

7. The method of claims 2,3,5 or 6 wherein $R_1$, $R_2$, $R_3$ and $R_4$ are the same or different unsubstituted alkyl, alkenyl or alkynyl radical.

8. The method of claim 7 wherein the total number of carbon atoms for $R_1+R_2$ and $R_3+R_4$ independently, are from about 8 to about 40.

9. The method of claim 8 wherein the extreme pressure enhancing amount is from about 0.25 to 15 weight percent of the total of compound and oleaginous material.

10. A method for enhancing the extreme pressure anti-wear characteristics of an oleaginous lubricating composition comprising admixing into said lubricating composition an extreme pressure anti-wear enhancing amount of a reaction product of 2,5-dimercapto-1,3,4-thiadiazole, an aldehyde and a primary or secondary, aliphatic or alicyclic amine reacted at a mole ratio of about 1:1:1 to about 1:2:2.

11. The method of claim 10 wherein the reaction product is further reacted with a metal or metal compound.

12. The method of claim 10 wherein the amine has from about 8 to about 100 carbon atoms.

13. The method of claim 10 wherein the amine has from about 8 to about 40 carbon atoms.

14. The method of claims 11, 12, or 13 wherein the aldehyde has from 1 to about 20 carbon atoms.

15. The method of claim 13 wherein the aldehyde has from 1 to about 10 carbon atoms.

16. The methods of claim 15 wherein the extreme pressure anti-wear enhancing amount is from about 2.25 to about 15 weight percent of the total amount of the compound and oleaginous material.

17. The lubricating composition as prepared by the method of claim 9.

18. A compound of the formula:

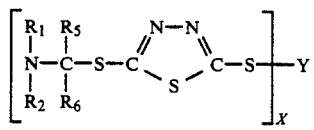

wherein:
X is 1 or 2;
Y is hydrogen, a Ia, IIa, or Ib series metal, a transition metal or an amino radical of the formula:

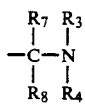

wherein:
$R_1$, $R_2$, $R_3$ and $R_4$ are the same or different and are hydrogen or a radical derived from an aliphatic or alicyclic compound with the total number of carbon atoms for $R_1+R_2$ and $R_3+R_4$, independently being from about 8 to about 100; and
$R_5$, $R_6$, $R_7$ and $R_8$ are the same or different and are hydrogen or an organic radical wherein the total number of carbon atoms for $R_5+R_6$ and $R_7+R_8$, independently is from about 0 to about 20, said compound having a solubility in oleaginous material of between about 2.25 and 15 weight percent of the total amount of compound and oleaginous material.

19. The compound of claim 18 wherein Y is hydrogen.

20. The compound of claim 18 wherein Y is the amino radical.

21. The compound of claim 18 wherein Y is sodium, potassium, magnesium or calcium.

22. The compound of claim 20 wherein the total number of carbon atoms for $R_5+R_6$ and $R_7+R_8$, independently, are from 0 to about 10.

23. The compound of claim 22 wherein $R_5$, $R_6$, $R_7$ and $R_8$ are a substituted or unsubstituted alkyl, alkenyl, alkynyl, aryl, aralkyl, alkyloxy, alkenyloxy, alkynyloxy, arakyloxy, aryloxy or aralkenyl radical.

24. The compound of claims 19, 20, 22 or 23 wherein $R_1$, $R_2$, $R_3$ and $R_4$ are the same or different unsubstituted alkyl, alkenyl or alkynyl radical.

25. The compound of claim 24 wherein the total number of carbon atoms for $R_1+R_2$ and $R_3+R_4$, independently, are from about 8 to about 40.

26. A reaction product of 2,5-dimercapto-1,3,4-thiadiazole, analdehyde, and a primary or secondary aliphatic or alicyclic amine reacted at a mole ratio of about 1:1:1 to about 1:2:2, said reaction product being soluble in oleaginous material at a concentration of between about 2.25 and 15 weight percent of the solution.

27. The reaction product of claim 26 wherein the reaction product is further reacted with a metal or metal compound.

28. The reaction product of claim 26 wherein the amine has from about 8 to about 100 carbon atoms.

29. The reaction product of claim 26 wherein the amine has from about 8 to about 40 carbon atoms.

30. The reaction product of claims 27, 28, or 29 wherein the aldehyde has from 1 to about 20 carbon atoms.

31. The reaction product of claim 30 wherein the aldehyde has from 1 to about 10 carbon atoms.

32. A lubricating composition comprising an oleaginous material and an extreme pressure, anti-wear enhancing amount of the compound of claim 18, 19, 20, 21, 22, or 23.

33. The composition of claim 32 wherein said oleaginous material is an internal combustion engine lubricating oil.

34. A lubricating composition comprising an oleaginous material and an extreme pressure, anti-wear enhancing amount of the reaction product of claims 26, 27, 28, or 29.

35. The composition of claim 34 wherein said oleaginous material is an internal combustion engine lubricating oil.

36. The reaction product of 2,5-dimercapto-1,3,4-thiadiazole, formaldehyde and a mixture of $C_{16}-C_{18}$ secondary amines reacted at a mole ratio of about 1:1:1 to about 1:2:2 at a temperature in the range of 25° C. to about 150° C. and a reaction time between about 0.5 and 40 hours.

37. The reaction product of 2,5-dimercapto-1,3,4-thiadiazole, formaldehyde and a mixture of $C_{16}-C_{18}$ primary amines reacted at a mole ratio of about 1:1:1 to about 1:2:2 at a temperature in the range of about 25° C. to about 150° C. and a reaction time between about 0.5 and 40 hours.

38. The reaction product of 2,5-dimercapto-1,3,4-thiadiazole, formaldehyde and tallowamines reacted at a mole ratio of about 1:1:1 to about 1:2:2 at a temperature in the range of about 25° C. to about 150° C. and a reaction time between about 0.5 and 40 hours.

39. A lubricating composition comprising an oleaginous material and an extreme pressure, anti-wear enhancing amount of the compound of claim 36, 37 or 38.

40. The composition of claim 44 wherein said oleaginous material is an internal combustion engine lubricating oil.

41. The compound of claim 18 wherein the lubricating anti-wear property is greater than 1,250-inch pounds according to ASTM Falex Test Method D2670-67 (reapproved 1977) when dissolved in a 450 neutral oil in a concentration of 2.25 weight percent.

42. The compound of claim 18 wherein the lubricating anti-wear property of said derivative is at least 1,875 inch-pounds according to said Test Method.

43. The compound of claim 18 wherein the lubricating anti-wear property of said derivative is at least 2,000 inch-pounds according to said Test Method.

44. The compound of claim 18 wherein the lubricating anti-wear property of said derivative is at least 3,500 inch-pounds according to said Test Method.

45. A lubricating composition comprising an oleaginous material and an extreme pressure, anti-wear enhancing amount of the compound of claim 42.

46. A lubricating composition comprising an oleaginous material and an extreme pressure, anti-wear enhancing amount of the compound of claim 43.

47. A lubricating composition comprising an oleaginous material and an extreme pressure, anti-wear enhancing amount of the compound of claim 44.

48. The method of claim 1 wherein said extreme pressure anti-wear enhancing amount is about 2.25 to about 15 weight percent based upon the total weight of oleaginous material and said extreme pressure anti-wear compound.

* * * * *

UNITED STATES PATENT AND TRADEMARK OFFICE
CERTIFICATE OF CORRECTION

PATENT NO. : 4,990,273

DATED : February 5, 1991

INVENTOR(S) : Michael C. Croudace

It is certified that error appears in the above-identified patent and that said Letters Patent is hereby corrected as shown below:

Claim 40, column 11, line 7, delete "44" and insert therefor -- 39 --.

Signed and Sealed this

Fifteenth Day of September, 1992

*Attest:*

DOUGLAS B. COMER

*Attesting Officer* — Acting Commissioner of Patents and Trademarks